(12) United States Patent
Marinelli

(10) Patent No.: US 7,412,275 B2
(45) Date of Patent: Aug. 12, 2008

(54) SUSCEPTOMETER FOR NON-INVASIVE IRON LEVEL MEASUREMENT IN A BODY

(76) Inventor: Mauro Marinelli, 2/1 Via Razeto, Genova (IT) 16132

( * ) Notice: Subject to any disclaimer, the term of this patent is extended or adjusted under 35 U.S.C. 154(b) by 0 days.

(21) Appl. No.: 10/538,411

(22) PCT Filed: Dec. 13, 2002

(86) PCT No.: PCT/EP02/14251

§ 371 (c)(1), (2), (4) Date: Aug. 14, 2006

(87) PCT Pub. No.: WO2004/055515

PCT Pub. Date: Jul. 1, 2004

(65) Prior Publication Data

US 2007/0161887 A1    Jul. 12, 2007

(51) Int. Cl.
*A61B 5/05* (2006.01)
*G01V 3/00* (2006.01)

(52) U.S. Cl. .................. 600/409; 600/410; 324/307

(58) Field of Classification Search .......... 600/309, 600/407, 409, 307, 410; 324/201, 248, 307
See application file for complete search history.

(56) References Cited

U.S. PATENT DOCUMENTS

2001/0011155 A1   8/2001   Rapoport
2002/0151779 A1   10/2002  Avrin et al.

FOREIGN PATENT DOCUMENTS

WO    0140790    6/2001

OTHER PUBLICATIONS

John H. Bauman, Richard W. Hoffman: "Magnetic Susceptibility Meter for In Vivo Estimation of Hepatic Iron Stores" Transactions on Bio-Medical Engineering, vol. 14, No. 4, Oct. 1967, pp. 239-243, XP001150027; Abstract; p. 241, left-hand column, paragraph 3—p. 242, left-hand column, paragraph 2; figures 2,3.
J. Steketee, H. Roggeveen, Y.J. Kingma: "Measurement of magnetic susceptibility in living rats" Meidcal & Biological Engineering & Computing, vol. 18, 1980, pp. 253-260, XP001150020; Abstract; p. 254, right-hand column, paragraph 1—p. 256, left-hand column, paragraph 1; figures 2-5.

*Primary Examiner*—Eric F Winakur
*Assistant Examiner*—Michael Rozanski
(74) *Attorney, Agent, or Firm*—Themis Intellectual Property Counsel

(57) ABSTRACT

A susceptometer for non-invasive determination of iron concentration in a body, by detecting the magnetic flux variation produced by the body. The susceptometer comprises a heat insulating case (16), containing a support structure that defines a screening region (8, 10). The structure supports an alternating magnetic field source, which is able to generate a magnetic field in the screening region, and at least two magnetic field sensors (4, 6), disposed in front of the field source (2). Means (12, 14) for introducing the body to be measured in the screening region (8, 10), temperature-control means, for stabilizing temperature inside the case, so as to limit relative variation to a predetermined maximum value, and means for processing electric signals indicative of the variation in the magnetic field linked to the sensor, which variation is caused by the screened body, in the screening region, are further provided.

31 Claims, 9 Drawing Sheets

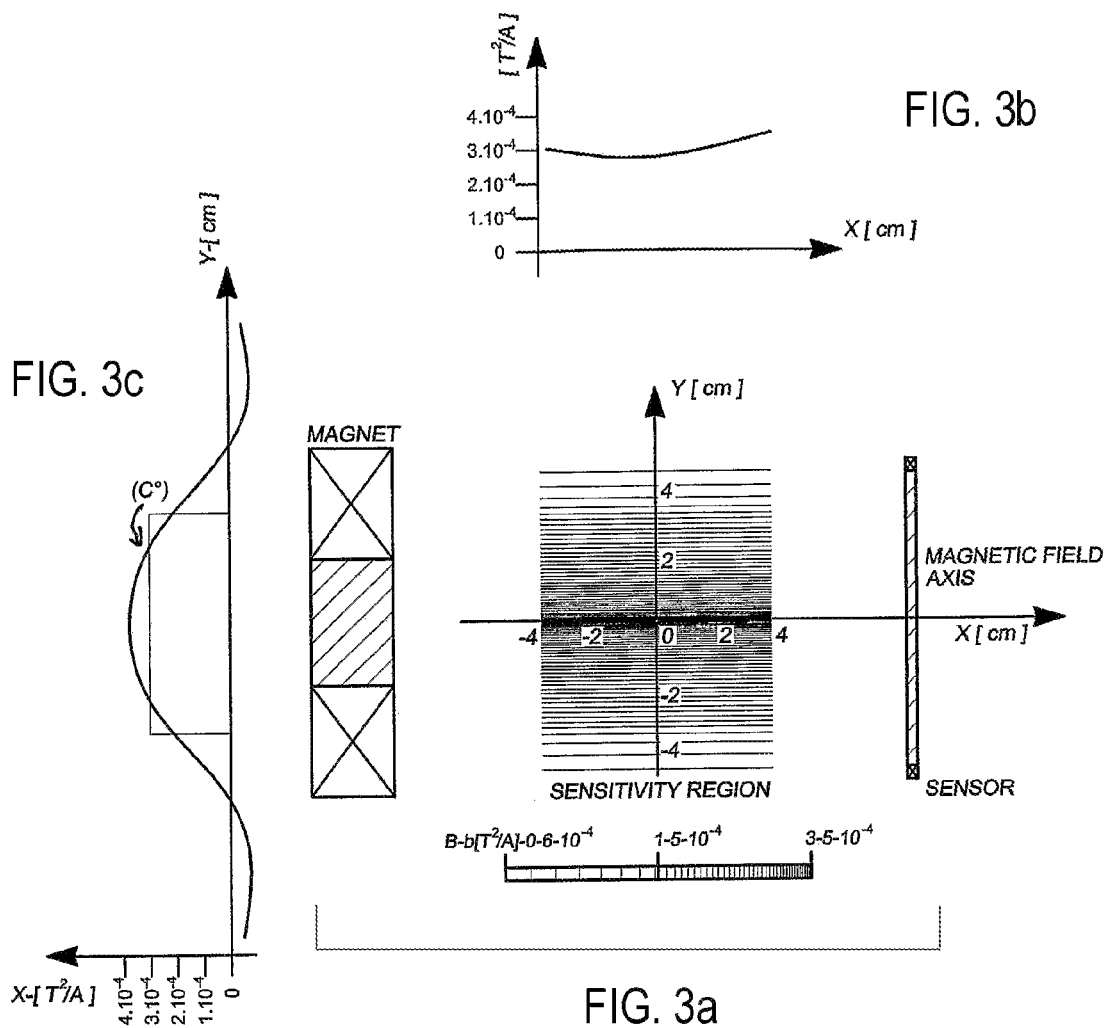
FIG. 3b
FIG. 3c
FIG. 3a
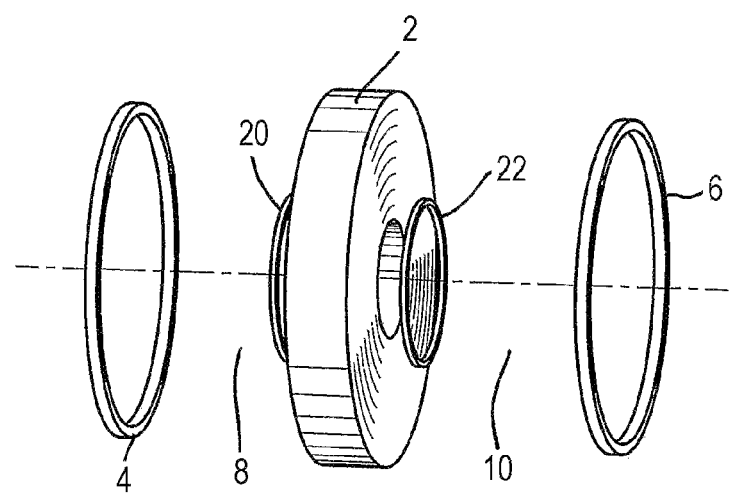
FIG. 7

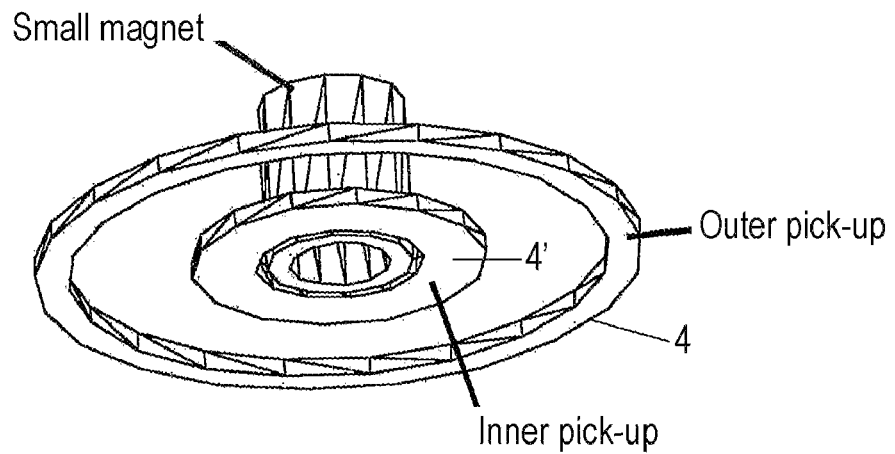
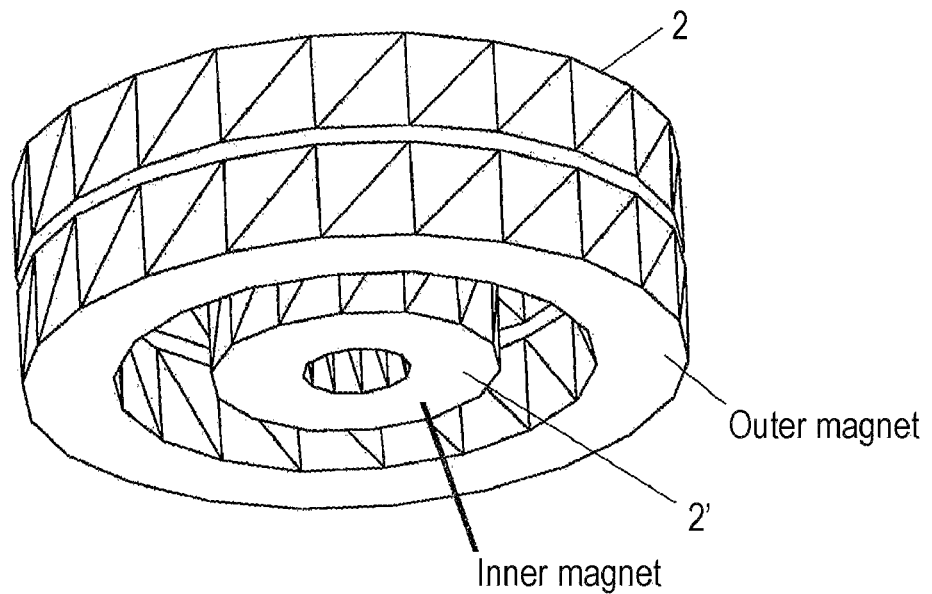
FIG. 16
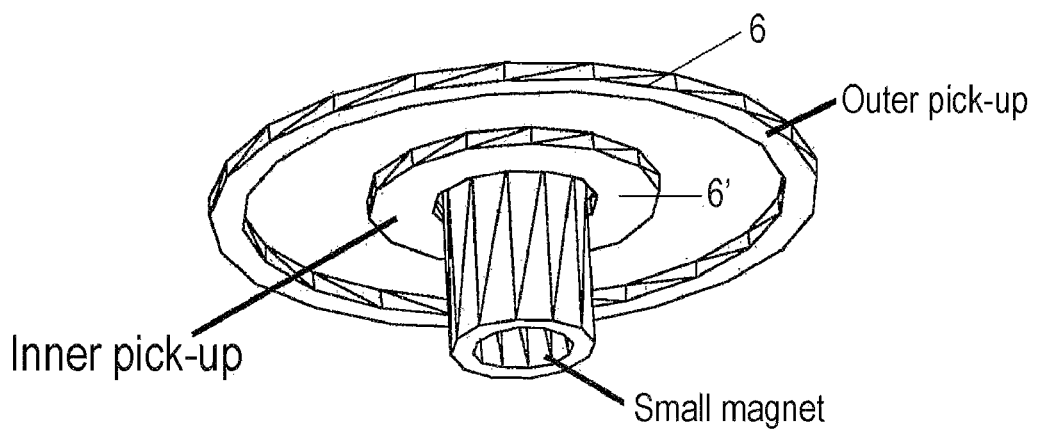

SUSCEPTOMETER FOR NON-INVASIVE IRON LEVEL MEASUREMENT IN A BODY

This invention relates to a susceptometer for non-invasive iron level measurement in a body, and particularly to a susceptometer which is adapted to determine iron concentration by detecting the magnetic field variation produced by the body.

A particular and advantageous application of the inventive susceptometer is non-invasive measurement of iron stores in the body of thalassemic patients.

Cooley's anemia (also known as beta-thalassemia major or thalassemia major) is a genetic hemolytic disease, resulting from a defective synthesis of hemoglobin. Individuals who suffer from this disease must undergo frequent blood transfusions in order to survive.

Since there is no natural way for the human body to eliminate iron, all iron contained in transfused red blood cells builds up and becomes toxic for tissues and organs. Any excess iron removal treatment requires the knowledge of iron concentration. At present, the most reliable method to quantify iron overload is chemical analysis of liver biopsy samples. The concentration of iron in the liver of an healthy individual is of a few hundreds of micrograms per cubic centimeter of wet tissue, and in ill persons it can even reach tens of milligrams per cubic centimeter. None of prior art non-invasive methods (concentration of serum ferritin, urinalysis after the administration of a chelating agent) is sufficiently accurate.

Several methods have been explored to make this measurement in a non-invasive manner and the most promising one seems to be biosusceptometry. At present, three susceptometers exists, in Hamburg (Germany), Cleveland (USA) and Turin (Italy). These apparatuses generate the magnetizing field by using a superconducting coil and read the field variations produced by the presence of the patient, by means of a superconducting gradiometer, connected to a SQUID. The magnetizing coil and the pick-up coil, both fitted on a quartz cylinder are at about the same position relative to the patient. Due to this geometry, the signal is highly dependent from the magnetic properties of the most superficial tissues. Also, the mechanical restrictions of cryogenic apparatuses do not practically allow to provide a suitable geometry for measuring iron overload in internal body parts.

An experimental instrument is known (IEEE Transactions on Biomedical Engineering, October 1967, p. 239), for room temperature iron level determination in a body, which substantially comprises a transformer that is cut in such a manner as to create a gap, wherein a body is positioned to be screened.

An improvement of this instrument is also known (Medical & Biological Engineering & Computing, 1980, Vol. 18, p. 253), which comprises thermal shields, designed to insulate the transformer from the heat radiated by the body being screened, and a cooling system to remove the heat accumulated on said thermal shields.

The above instruments include a measuring circuit, comprising a field source and a sensor, which is designed to transmit a signal derived from the presence of the body in the screening region, and a reference circuit, comprising a field source and a sensor independent from those of the measuring circuit, which is designed to transmit a reference signal.

The document Medical & Biological Engineering & Computing further describes an apparatus, in which the transformer is replaced by a solenoid structure. This structure includes an outer primary winding, for generating a uniform magnetic field inside it, an inner measuring secondary winding and an inner reference secondary measurement, the two secondary windings being coaxial with the primary and symmetric with respect to a transverse median plane of the solenoid. The measuring winding is designed to detect a variation in the linked magnetic flux, caused by the presence of a body in the screening region that is internal with respect to said winding, whereas the reference winding provides a reference signal.

In all the above equipment, measurement results are derived from the difference between the signal generated by the screened body and the reference signal.

Nevertheless, these room temperature instruments cannot reach such a sensitivity as to allow in vivo quantification of iron overload in a body. Particularly, thermal expansion of the apparatus, which is caused by the presence of a body in the relevant area, perturb the measurement signal and the test signal to different extents, thereby causing an additional signal degradation deriving from the difference therebetween.

According to the invention, this problem is solved thanks to a susceptometer in which the measuring sensor and the reference sensor receive signals generated by the same field source, and in which temperature control is further provided to reduce any structural deformation which might change the shape or position of a sensor relative to another or to the field source, thereby reducing the possibility of a difference of spurious signals for the measuring sensor and the reference sensor.

Therefore, the object of the invention is a susceptometer as mentioned hereinbefore, characterized in that it comprises:

a heat insulating case, containing a support structure, which is made of a non-magnetic and electrically insulating material, and operationally kept substantially at room temperature, and which defines a screening region;

an alternating magnetic field source, supported by said structure and able to generate a magnetic field in said screening region;

at least two magnetic field sensors (pick-up coils), supported by said structure and disposed in front of said field source;

means for introducing the body to be screened in the screening region defined by said field source and at least one of said at least two sensors;

temperature control means, for stabilizing temperature inside said case, at least during measurement, in such a manner as to limit relative variation to a predetermined maximum value, so that thermal expansion of the support structure and the associated field source and sensors are substantially ininfluent on the magnetic field flux linked with said at least two sensors; and means for processing electric signals indicative of the variation in the magnetic flux linked with said at least two sensors, which variation is caused by the presence of the body being screened, in the screening region.

Several embodiments and further improvements of the invention will form the subject of the subclaims.

Further advantages and characteristics of the inventive susceptometer will be apparent from the following detailed description, referred to the accompanying drawings, which are provided as non-limiting examples, in which:

FIG. 3 is a diagram showing the values of a quantity related with the geometry of the magnet and sensors of the apparatus as shown in FIG. 1;

Figure 4:
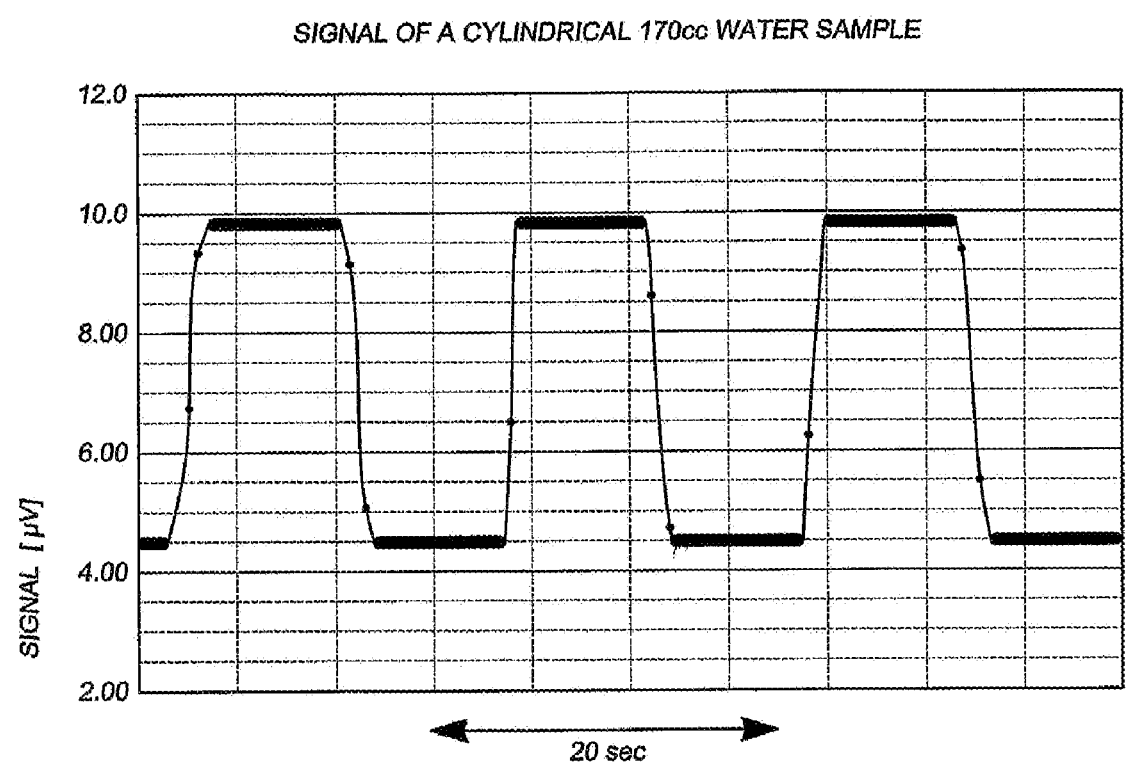
Figure 12:
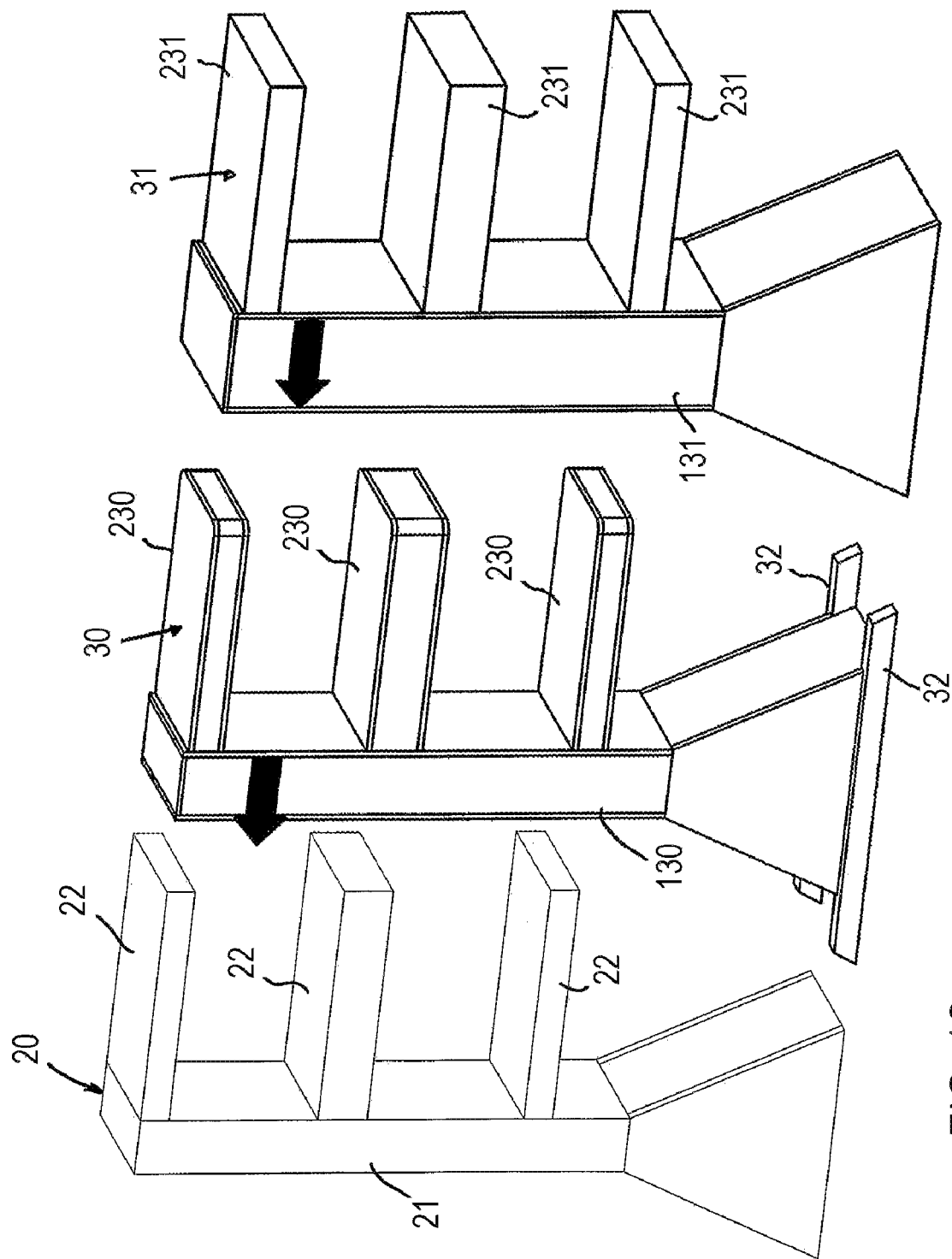
Figure 13:
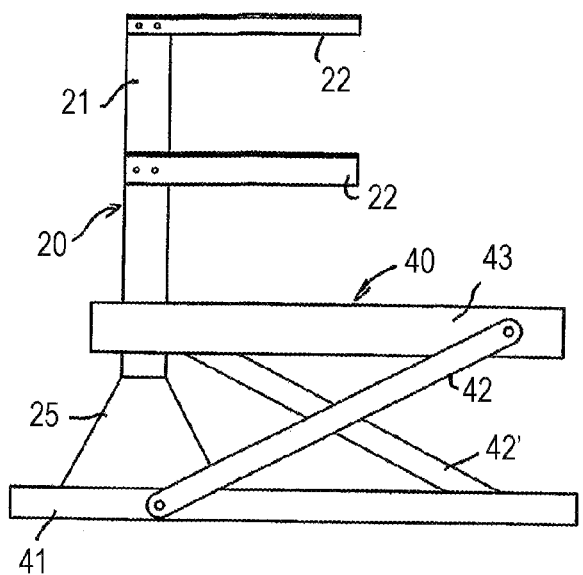
Figure 14:
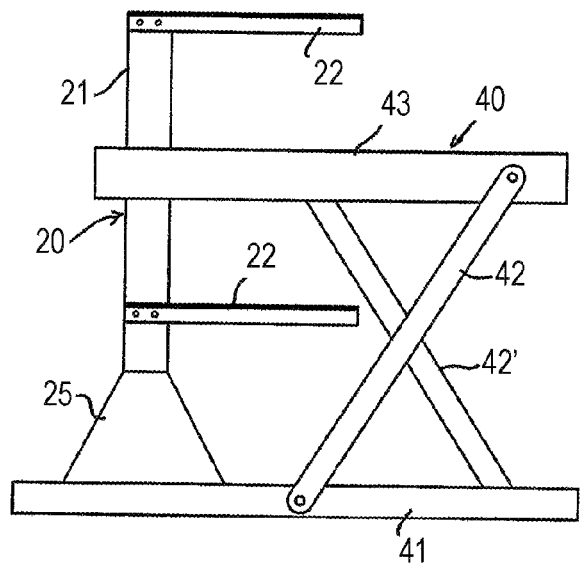

FIGS. 4.-5-6 are diagrams showing the results of measurements performed with the help of a prototype of the inventive susceptometer;

FIG. 7 is a perspective schematic view of the arrangement of the magnet and sensors of an improved embodiment of the inventive apparatus;

FIGS. 8 to 11 are different views of a structure for supporting the magnetic field source and the field sensing pick-ups, which is particularly suitable for analyses on human beings;

FIG. 12 is an exploded perspective view of the support structure and the two shell covers thereof for generating a diathermic liquid flow designed to stabilize the temperature of the support structure;

FIGS. 13 and 14 are two views of a patient table and the susceptometer as shown in the preceding FIGS. 8 to 12, with the table in the two different patient insertion-positions, i.e. between the lower pick-up and the central magnetic field source and between the upper pick-up and the central magnetic field source.

Figure 15:
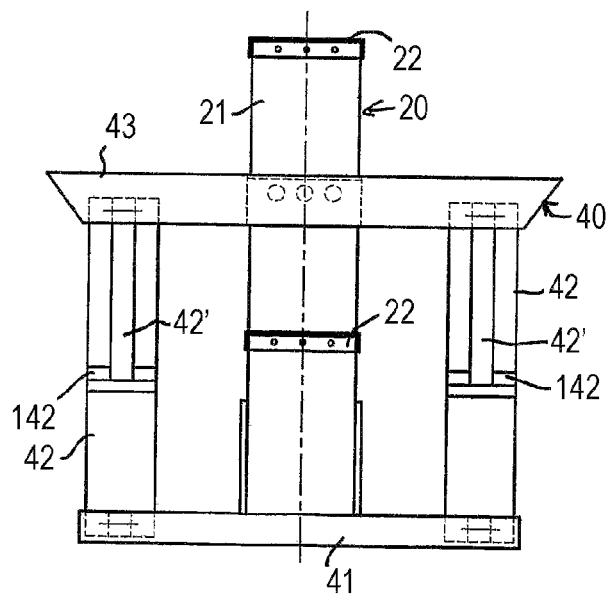

FIG. 15 is a view taken from the table end side of the table and susceptometer assembly as shown in FIG. 14.

FIG. 16 is a schematic view of a variant embodiment of the combination of a magnetic field source and the pick-ups, in which all the other construction parts have been omitted.

The following description is referred to a prototype of a susceptometer according to the invention, for measuring relatively small samples, and of a large susceptometer, for measuring iron stores in the body of a human being.

The construction principle is based on the following considerations. Molar susceptibility of iron in ferritin-hemosiderin (iron stores being found in the form of these molecules) is of $+8.2 \cdot 10^{-8}$ m$^3$ mole. For instance, an iron overload of 0.6 mg/g in an organ reduces the diamagnetic susceptibility thereof by 10%; this iron concentration adds a paramagnetic contribution of $+0.9 \cdot 10^{-6}$ to the susceptibility of a normal organ, which is similar to that of water (the susceptibility by unit of volume in the international system is nondimensional: in the same units, diamagnetic susceptibility of water is of $-9.0 \cdot 10^{-6}$). One of the methods to determine magnetic susceptibility of a body is introducing it in a magnetic field and measuring the field variation caused by the body; for instance, the magnetic field in the proximity of a spherical (diamagnetic) water sample is about 9 parts per million smaller than the uniform magnetic field applied to the sample. In order to measure relevant iron concentrations which, as mentioned above, produce susceptibility variations of the order of one tenth of water susceptibility, the susceptometer shall be able to detect magnetic field variations of at least one part per 10 millions. Relative magnetic field variation ($\Delta$B/B) in the proximity of a weakly magnetic sample introduced in a uniform exciting field is proportional to the magnetic susceptibility of the sample. As is apparent, the proportionality of susceptibility to relative field variation allowed to give up the high absolute sensitivity of SQUIDs and to provide an apparatus with no low-temperature devices.

Figure 1:
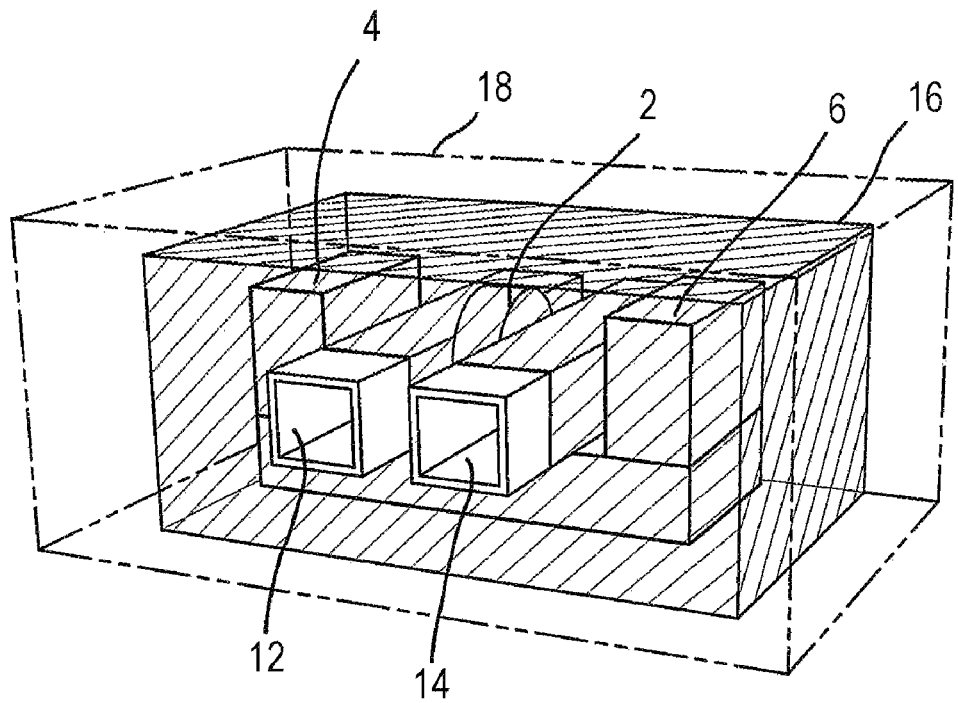
FIG. 1 is a perspective schematic view of an apparatus according to the invention.
Figure 2:
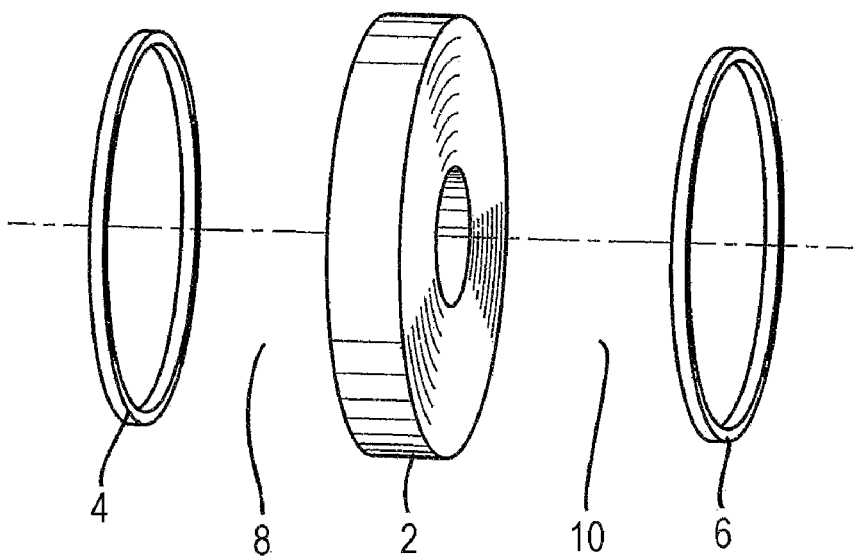
FIG. 2 is a perspective schematic view of the arrangement of the magnet and sensors of the apparatus as shown in FIG. 1.

As shown in FIGS. 1 and 2, the susceptometer comprises a magnetic field source 2, e.g. formed by a magnetizing coil adapted to generate an alternating magnetic field. Numerals 4 and 6 denote the two sensors (pick-up coils), disposed symmetrically with respect to the magnetic field source 2.

The field source 2 and the pick-up coils 4, 6 are mounted on an electrically insulating and weakly magnetic support. While the support structure of the Figure is made of plates, supports may be also provided that have a lighter structure, e.g. a tubular shape. The sensitivity of the apparatus is mainly limited by the mechanical stability of this structure, i.e. of spurious magnetic flux variations in pick-up coils, caused by deformations of the structure and/or by the geometry of the magnet and the pick-up coils.

Two screening regions 8, 10 are defined between the magnetic field source 2 and the transducers 4, 6: in order to make measurements, the sample is introduced in one of the two regions and heat-insulated from the apparatus by means of two insulating, non-magnetic tunnels 12, 14.

The apparatus further has a first insulating casing 16, which encloses the support structure and has apertures for sample receiving tunnels. Preferably, the casing 16 is in turn enclosed in a second insulating case 18. Both cases 16, 18 are made of a weakly magnetic material.

The apparatus further has temperature control means (not shown), which are designed to stabilize temperature inside the casing 16, so that, at least during measurements, the thermal expansion of the structure supporting the associated magnetic field source 2 and the sensors 4, 6 are substantially non-influent on the variation in the magnetic flux linked with the sensors. These temperature control means may include a plurality of non-magnetic heating elements, associated to the support; to this end, carbon resistors may be used, of the type known as Allen Bradley resistors.

Temperature control means further include temperature sensors for measuring the temperature of the support in the proximity of each heating element and a feedback control system, to keep the measured temperature constant to a few thousandths of degree. Preferably, the control means also include one or more heating/cooling elements, associated to the walls of the case 16 or 18 or both, which are designed to control the temperature of the environment around the enclosure 16. For instance, coils with a diathermic fluid, like cold water, flowing therein, may be embedded in the walls of the case 18. Here again, the diathermic fluid flow will be controlled as a function of the temperature detected by temperature sensors. Thermal control is further refined, by also associating temperature control means to the walls of tunnels 12 and 14, so that—once a hot sample is introduced therein—those control means are activated to prevent any undesired temperature perturbation.

Finally, the apparatus has means for processing electric signals indicative of the variation in the magnetic flux linked with the sensor, which variation is caused by the presence of the screened body. Those processing means include a lock-in amplifier, which reads the difference between the signals detected by the sensors 4 and 6. The arrangement and connection of sensors is such that, when no sample is inserted, the signal read by the lock-in amplifier is null.

During screening operations, the sample is moved in and out of the screening region (either the region 8 or the region 10) several times, each insertion of the sample producing a dominant flux variation in the sensor (pick-up coil) adjacent to the sample (sensor 4 for the screening region 8 and sensor 6 for the screening region 10). A computer records the signal, in synchronism with the insertion and exit of the sample; this additional synchronous detection allows measurement to be independent from the little drift that is still present, in spite of the above described temperature control. Equation 1 below is used to determine the contribution to the magnetic field flux, linked with the pick-up coil, due to the presence of the sample:

$$\phi = \frac{-}{\mu 0} \int_{Volume} \aleph(r) B \cdot b \cdot dr \qquad (1)$$

where $\mu_0$ is vacuum magnetic permeability, $\chi(r)$ is the magnetic susceptibility of the material, B is the exciting magnetic field and b is the magnetic field which would be generated by the pick-up if a unit current flew across it; the integral is calculated on the sample volume.

Referring now to FIG. 3, the two-dimensional diagram a) shows, in a gray scale, the values of the inner product (B·b), related with the magnet-sensor geometry, in the region between the exciting magnet and one sensor: darker areas denote a positive inner product and a higher intensity, brighter areas denote a decreasing intensity until the inner product reaches negative values. It may be noted that this inner product is generally not uniform in space, and varies in terms of both intensity and sign. As is apparent from equation 1, the magnetic field, hence the sensitivity of the instrument, depends from the product (B·b). The region of space (hereafter sensitivity region), in which this product is substantially other than zero, has the shape of a cylinder which is coaxial with the field and in one specific embodiment, has a diameter of about 6 cm and a volume of 200 ml. In diagram b), the inner product (B·b) is shown as a function of the position x on the axis of symmetry of the magnetic field. In diagram c), the inner product (B·b) is shown as a function of the radial position y on an axis equidistant from the magnet and the sensor.

FIG. 4 shows the signal produced by the repeated insertion and extraction of a 170 cc water sample, contained in a plastic container, in and from the apparatus. It shall be noted that, in this specific embodiment, the contribution of a water sample, integrally contained in this region, to the signal, is of −30 nV/g, whereas the contribution of a sample outside the region is substantially null. The water sample signal increases with the sample volume. The magnetic field in the sensitivity region is no higher than a few tens of Gauss and oscillates at a frequency of a few hundreds of Hz.

Once the signal per unit of volume produced by the above water sample (−30 nV/g) and the susceptibility of ferritin-hemosiderin (+8.2·10$^{-8}$ m$^3$ mole) are known, 1 mg of iron (ferritin-hemosiderin) container in the sensitivity region may be determined to produce a signal of 4.9 nV. Due to the 25 nV noise affecting the measurement, the minimum amount of iron (ferritin-hemosiderin) inside the sensitivity region, detectable by the susceptometer is of 5 mg. This means that average iron concentration measuring sensitivity in a sample, whose volume occupies the whole sensitivity region (200 cc for this susceptometer), is of 0.025 mg/ml. For instance, in a water sample of 170 g, the sensitivity of the apparatus allows to detect a susceptibility variation of 0.5%, which is equivalent to an iron concentration variation of 0.030 mg/g (see FIG. 4). Iron concentration measuring sensitivity worsens as the sample volume decreases.

An instrumental noise of 25 nV is about 3 parts per 10$^8$ of the signal at the ends of each sensor. It shall be noted that, in order to detect relative field variations below one part per 10$^7$, relative variations in the susceptometer size, during the measuring step, shall be of the same order of magnitude or lower: the susceptometer of the invention allows to reach this result.

Figure 5:
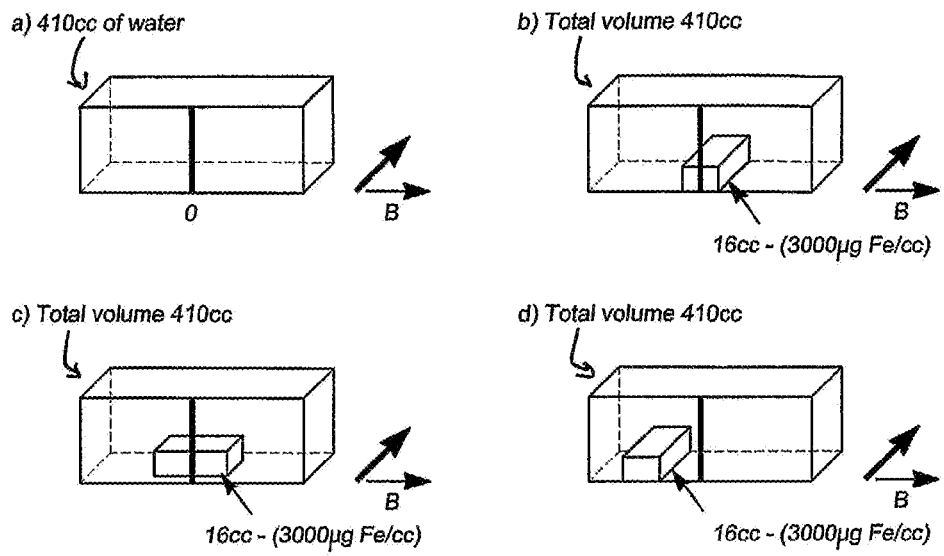
Figure 5:
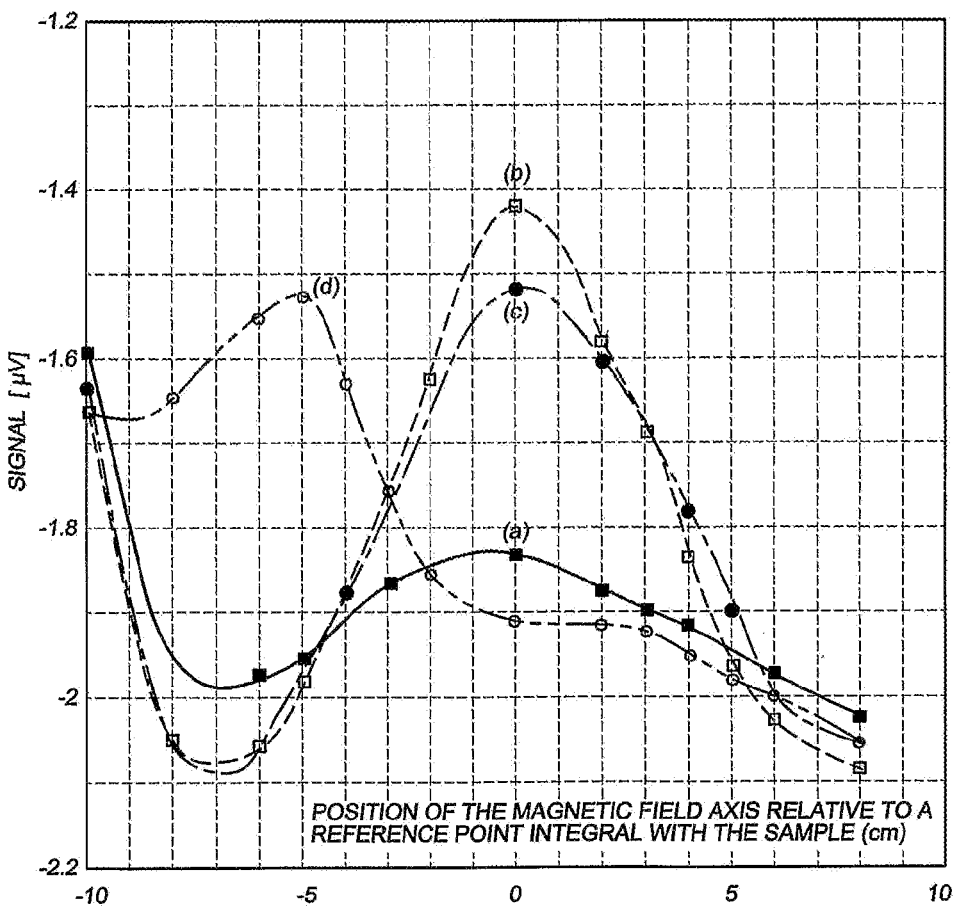
Figure 5:
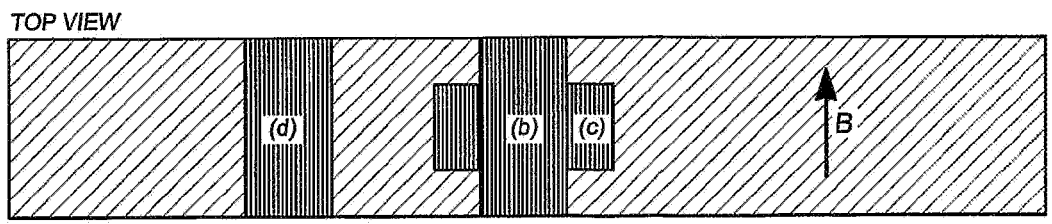
Figure 6:
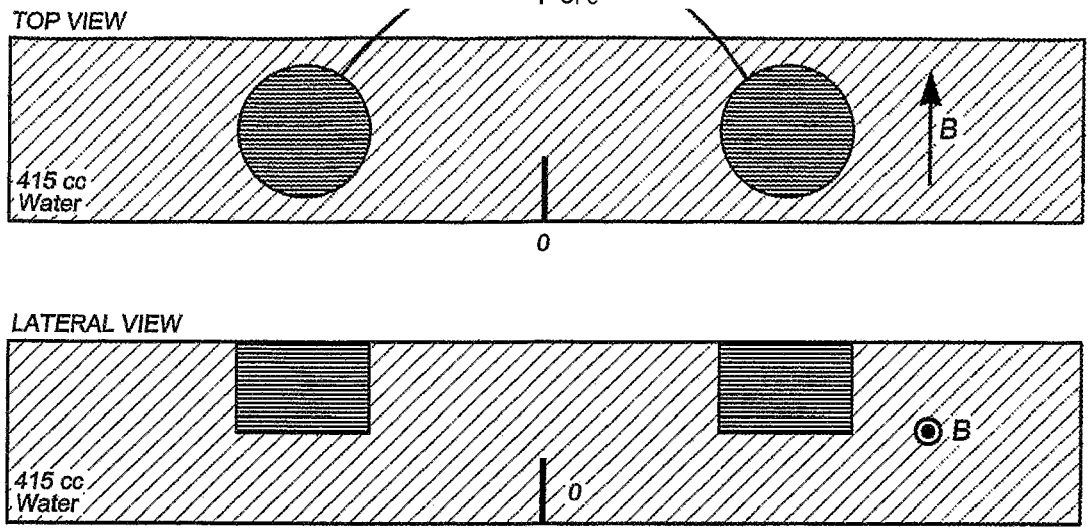
Figure 6:
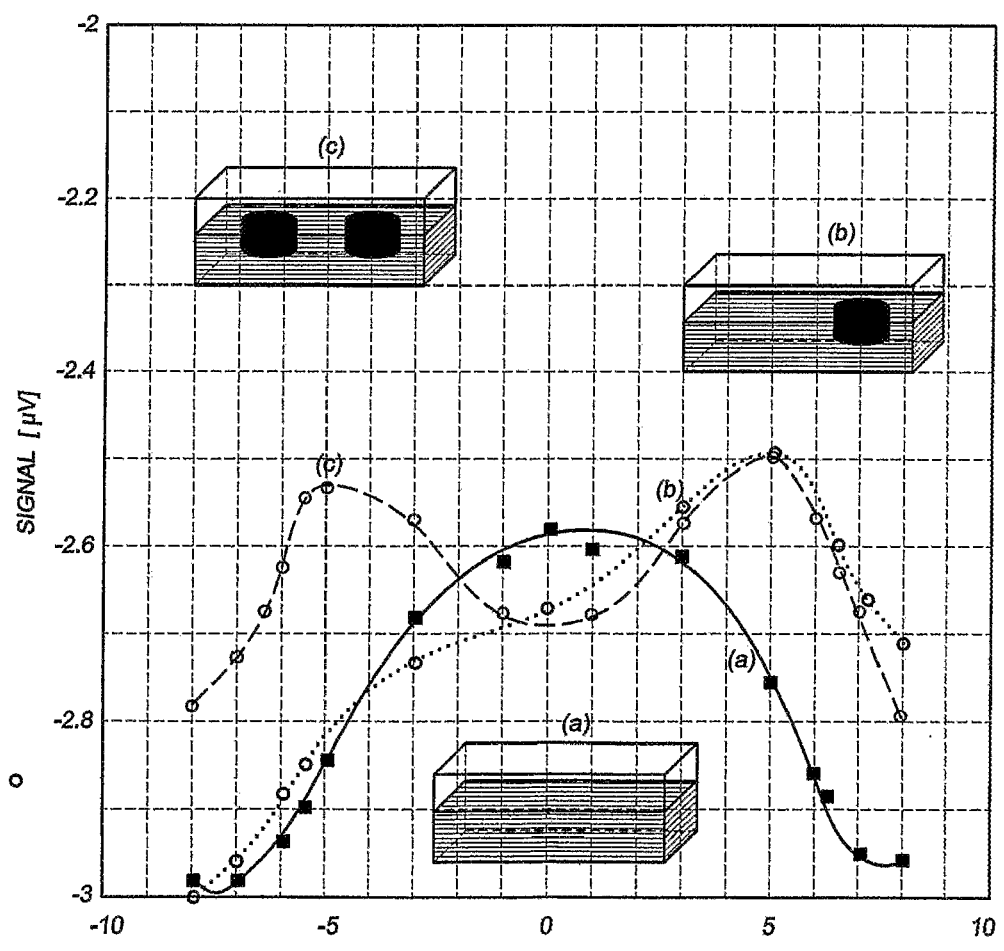

With reference to the diagrams of FIGS. 5 and 6, it may be noted that the spatial inhomogeneity of the inner product (B·b) allows to obtain different signals depending on the location of a sample relative to the sensitivity region. In fact, the diagrams of these figures show the curve of the signal detected by the apparatus as a function of the sample position in the screening region with reference to a neutral axis (0 position), corresponding to the median axis of the region, relative to a sample with an inhomogeneous arrangement of iron ions. The sample is contained in a prismatic plastic case, having a volume of about 410 cc. In diagram of FIG. 5: curve a) is related to a demineralized water sample; curves b), c) and d) are related to the signal generated by samples that contain, inside the main casing, a second case with 16 cc of an iron ion solution with a concentration of about 3000 $\mu g_{Fe}/cc$; in the three curves b), c) and d), the secondary case is positioned in different regions of the main case, to create a sample with an inhomogeneous iron distribution. In the diagram of FIG. 6: curve a) is related to a demineralized water sample; curve b) is related to the signal generated by a sample that contains, inside the main casing, a second case with 16 cc of an iron ion solution with a concentration of about 3000 $\mu g_{Fe}/cc$; and curve c) is related to the signal generated by a sample that contains, inside the main casing, two cylindrical cases, each containing about 16 cc of an iron ion solution with a concentration of about 3000 $\mu g_{Fe}/cc$.

FIGS. 5 and 6 clearly show that this specific embodiment of the apparatus has a spatial resolution of about 2 cm, i.e. it may resolve iron accumulations at a distance of more than 2 cm from each other.

In accordance with an improved embodiment, which is shown in FIG. 7, in the proximity of the field source 2 two additional sensors 20, 22 are mounted in symmetrical positions with respect to the source 2. The additional sensors 20, 22 are disposed in such a manner that the variation in the magnetic field fluxes linked therewith, caused by the presence of a body in the sensitivity region, is substantially a function of the magnetic properties of the outermost areas of this body only. Hence, the measuring configuration of FIG. 7 allows to determine the magnetic properties of the inner region of the sample, by subtracting, with an appropriate weight, the signal produced by the sensors 20, 22, from the signal produced by the sensors 4, 6.

An advantageous embodiment of the susceptometer as shown in the preceding FIGS. 1 to 7 also has, alternatively to or in combination with the foamed tunnels 12 and 14, a gap for feeding a flow of diathermic liquid, particularly water, at a controlled temperature. In fact, the heat given to the apparatus by the screened body, which is accommodated in the foamed tubular chambers, was found to have a detectable effect, which causes a signal drift, due to infinitesimal variations of the structure supporting the magnetic field generator and the magnetic field sensors.

The diathermic temperature-controlled liquid flow removes the heat generated and introduced in the susceptometer structure by the body being screened.

An additional variant consists in removing both the foamed tubular members, and the casing 16 of the embodiment described with reference to FIG. 1.

Here, the susceptometer structure is housed in a case whose shape corresponds to the structure of the assembly composed of the supporting members, the magnetic field source and the magnetic field sensing pick-ups and the case has a two-shell conformation, in which a liquid-tight gap is formed, having at least one feed inlet and one drain outlet, to obtain a diathermic fluid flow, which surrounds at least the most relevant parts or substantially the whole structure of said assembly composed of the support structure, the magnetic field source, and the magnetic field sensing pick-ups. This construction configuration has the advantage of reducing the size of the device, thanks to the removal of the casing 16 as shown in FIG. 1 and of avoiding the use of foamed tunnels 12 and 14, which is desirable in apparatuses designed for examinations on human beings. Also, the temperature of the susceptometer may be stabilized thanks to a feedback control of the fluid around it. Magnet temperature is itself measured with a high sensitivity, and controlled by a feedback system, which modulates the temperature of water flowing through the hollow copper conductors that form magnets.

In one embodiment of the invention, as shown in FIGS. 8 to 15, to be intended as an alternative to the embodiment of FIG. 1, and particularly adapted to examinations on human beings, the susceptometer has a support structure 20, including an upright 21 with three vertically aligned cantilevers 22 which project on the same side and support the two magnetic field sensing pick-ups and the magnetic field source respectively, in the above specified order, i.e. with the magnetic field source between the two magnetic field sensing pick-ups.

Figure 10:
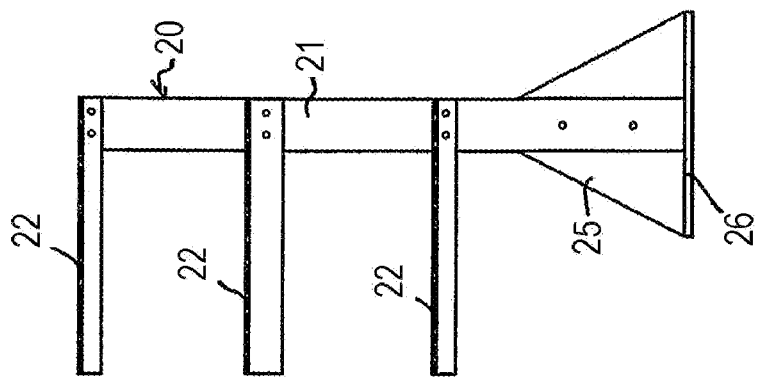
Figure 11:
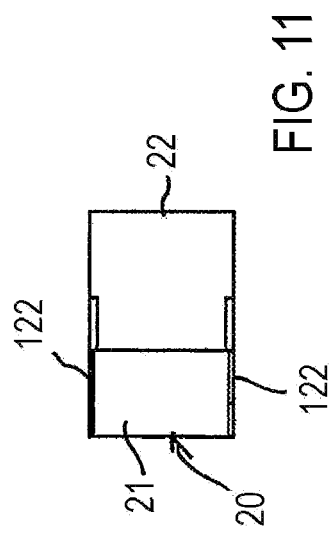

The upright 20 has the shape of a hollow panel or rectangular beam as is apparent from the vertical cross section of FIG. 10 and from the top plan view of FIG. 11.

The cantilevers 22 are themselves provided as hollow panels adapted to receive the pickups and the magnetic field source respectively, not shown in detail in FIGS. 8 to 11. At the end attached to the upright 21, the panels have fastening tabs 122, which are provided as extensions of the vertical side walls, abutting against the corresponding opposite sides of the upright 21. The tabs are fastened with the help of dowels and fast pins, which are denoted as 23 and 24 respectively.

A trapezoidal base member 25 for each side wall of the upright 21 acts as a reinforced fastener between said upright 21 and a base plate 26.

Figure 9:
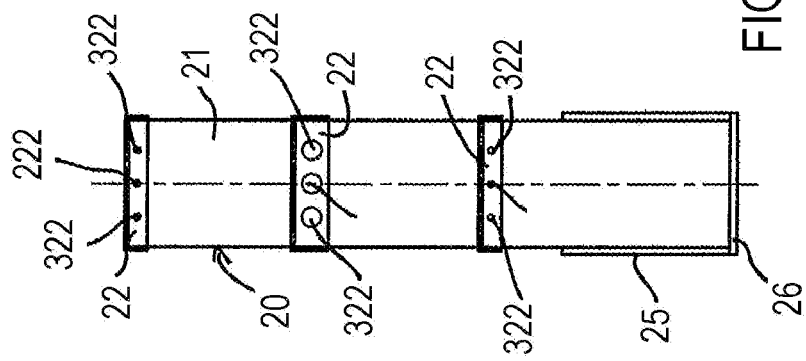
Figure 8:
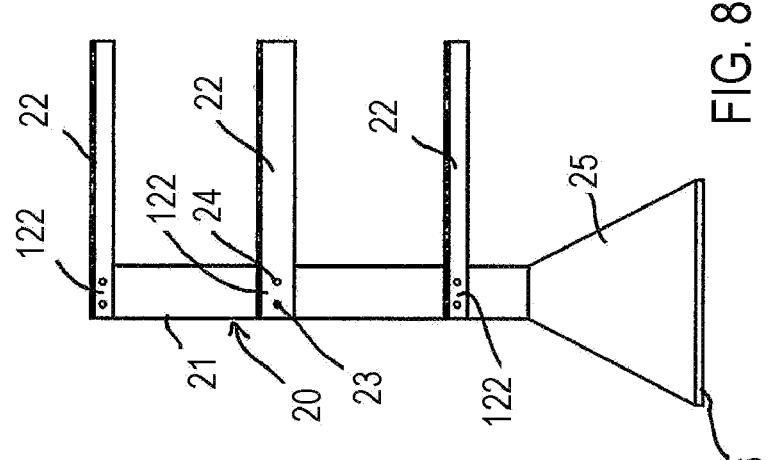

As is apparent from FIG. 9, holes 222 and 322 are formed at the end sides of the cantilevers 22, for the insertion of dowels, and fast pins respectively, to secure the magnetic field source and of the pick-ups in the corresponding cantilever.

The structure 20 is made of a non-magnetic material, for instance plastic or fiber-reinforced resin, for instance glass reinforced plastics.

Therefore, the structure 20 has a vertical comb shape.

Referring now to FIG. 12, said structure 21 with its pick-ups and the magnetic field source and possibly with sensors and leads for connection with other required construction members are housed in a first inner shell 30 having a corresponding shape and in another outer shell 31, also having a corresponding shape, but such a size as to form a gap for the flow of the above generally described diathermic liquid between the inner shell 30 and the outer shell 31, which are joined together at the rear side and at the base plate to form a gap which is liquid-tight towards the outside of the outer shell 31 and the inside of the inner shell 30. Obviously, the gap communicates with a diathermic fluid feed and drain line through inlets and outlets not shown in detail.

As is apparent from FIG. 12, the two casings with different sizes have a portion 130, 131 which is adapted to receive the upright 21 and cavities 230, 231 for receiving the cantilevers 22. The cavities 230, 231 communicate with the cavities 130, 131 of the upright 21 of the support structure 20, whereas the latter increases in width as it gets closer to the bottom portion, as a trapezium, to form the housing cavity of the trapezoidal base of the support structure. Advantageously this cavity of the trapezoidal base provides a better stability to the structure and other support members 32 may be associated thereto, such as side cross members which, if designed with a tubular shape, may also form inlets and outlets for the diathermic flow, besides improving themselves stability of the whole structure.

The distance between the central magnetic field source and the two pick-ups disposed on opposite sides of the magnetic field source, i.e. between the corresponding cantilevers 22 is such as to allow the introduction of the patient body or a patient table or stretcher between said magnetic field source and one of the two opposite pick-ups.

Advantageously, the stretcher is fitted on a frame that may be lifted and lowered to allow vertical motion of the supporting surface of the table or stretcher, until it reaches the height whereat the stretcher with the patient body on it may be introduced either in the space between the upper pick-up and the intermediate magnetic field source or in the space between said intermediate field and the lower pick-up. At the junction with the cantilevers, the stretcher may have a recess, whose size and shape substantially correspond to those of the cantilevers or an aperture coinciding with the body part to be screened, typically the liver.

FIGS. 13 to 15 show a patient table combined with the inventive susceptometer. The table 40 is shown in FIGS. 13 and 14 in its two operating positions. The table structure is composed of a surface for supporting the body under examination, possibly having a recess whose shape is complementary to the cantilever shape, and in which either the cantilever with the lower pick-up (FIG. 13) or the one with the magnetic field source (FIG. 14) may penetrate, in the operating condition, to carry the body part to be screened in the proper position, in line with the pick-ups and with the magnetic field source.

It shall be noted that the patient does not need to be moved relative to the stretcher or table 40, and always keeps its position through the two or more different measuring steps, thereby simplifying data analysis.

It shall also be noted that the same patient turns his/her back or abdomen to the magnetic field source depending on his/her insertion in the space above or below the magnetic field source. In these conditions, several measurements may be made, particularly at least two measurements, each with a different patient orientation with respect to the three magnetic field sources, hence the three magnetic fields generated thereby. Also, when two different magnetic field measuring pick-ups are used (FIG. 16), 12 measurements may be made for each patient position relative to the magnetic field axis, and this allows for a simpler determination of excess iron stores in the body and of the distribution thereof.

With reference to the embodiment as shown in FIGS. 13 to 15, the table or stretcher is supported by a member composed of jointed arms, which allows the table or stretcher to be positioned at different heights.

In the embodiment as shown in FIGS. 13 to 15, the lower ends of four lifting arms 42 are jointed to a base of the table 40 which acts as a trolley 41. An arm 42 is provided on each transverse side of the table, and is jointed at its ends to the base 41 and to the body supporting surface 40 respectively. The axes of articulation of the two arms 42 are coincident. A second arm 42' for each jointed arm 42 is in turn jointed to the base 41, but it is free to run to the upper end toward the plane defined by the arm 42' and passes through an aperture 142 of the arm 42. Abutment means are provided along the arm 42, which engage with the edges of the aperture 142 and allow the surface to be locked in position, preventing the table to be lowered unless it is previously released by a slight lifting action. These systems are well-known and any surface lifting and lowering arrangement may be used.

The base 41 and the patient supporting surface 43 overhang from the structure side 20, that carries the magnetic field source 2 and the pick-ups 4, 6, the arm system 42, 42', being eccentric with respect to said two surfaces.

Nevertheless, in combination with the means for lifting and/or lowering the body supporting surface (43), removable means are provided for locking this body supporting surface (43) in position.

It shall be noted that all the structural support members of the apparatus and table, as well as the shells that form the susceptometer case are made of a non-magnetic material, particularly glass-reinforced plastics or the like.

A further embodiment of the magnetic field source and the pick-ups is shown in FIG. 16. In this embodiment two magnetic field sources 2 and 2' are provided, having different extensions, and hence being able to generate magnetic fluxes in a larger volume and in a smaller volume. In this case, two pick-ups 4, 4' and 6, 6' are provided on each side of the two magnetic field sources 2, 2', and in line therewith, to sense the magnetic fields generated by the larger source 2 and by the smaller source 2'.

Here, the two sources 2, 2' are made of two circular annular superconducting coils, with hollow copper conductors, which are coaxial and concentric. Similarly, the pick-ups 4, 4' and 6, 6' of the two pairs of pick-ups are made of coaxial and concentric circular annular coils, whose positions are axially coincident with the corresponding magnetic field generating coil for said two sources 2, 2'. In order to minimize the stray capacity of pick-ups, the latter are formed of several superposed printed circuit layers.

An additional magnet may be positioned coaxially inside the inner pickups 4' and 6'.

Thanks to the three magnetic field sources and to the concentric pick-ups, 12 measurements may be made, as mentioned above, for each patient position relative to the magnetic field axis, and this allows for a simpler determination of excess iron stores in the body and of the distribution thereof.

This invention shall not be intended to be limited to the embodiments described and illustrated herein, which are to be considered as implementation examples only; the invention is subject to modification, as regards shape, arrangement of parts, construction details and operation. For instance, the possibility of providing several magnetic field geometries might suggest the attempt to design a geometry in which the inner product (B·b) is distributed with a relatively high gradient in the heart region, and in which the magnetic properties of this organ might be obtained by synchronizing magnetic signal detection with heart beats.

The invention claimed is:

1. A susceptometer for non-invasive iron level measurement in a body comprising:
   a first heat insulating case comprising a support structure, the first case being made of a non-magnetic and essentially insulating material;
   an alternating magnetic field source generating a magnetic field within the first case, the source being supported by the structure;
   a first and a second magnetic field sensors supported by the structure and disposed on opposite sides of the source, a first screening region being interposed between the source and the first sensor and a second screening region being interposed between the source and the second sensor, the temperature within the first and the second screening regions being controlled by limiting variations of the temperature to a predetermined maximum value;
   means for disposing the body within the first or the second screening region; and
   means for processing electric signals perceived by the first or second sensors, the signals being indicative of a variation in the magnetic field caused by the body in the first or second screening regions.

2. The susceptometer of claim 1, wherein the first and the second sensors are disposed symmetrically with respect to the source.

3. The susceptometer of claim 1, further comprising a third sensor disposed between the source and the first sensor and a fourth sensor disposed between the source and the fourth sensor, the first screening region being interposed between the first and the third sensor and the second screening region being interposed between the second and the fourth sensors.

4. The susceptometer of claim 1, further comprising a second heat insulation case disposed around the first heat insulating case.

5. The susceptometer of claim 1, wherein the means for disposing the body comprise a first and a second tunnels, wherein the first and the second tunnels have insulating non-magnetic walls, and wherein the first and the second tunnels each include at least one opening for introducing the body.

6. The susceptometer of claim 5, wherein the temperature is controlled by providing a plurality of heating/cooling members coupled to the first and the second tunnels and by further providing temperature sensors for sensing the temperature, and wherein the temperature is adjusted by the heating and cooling members according to measurements by the temperature sensors.

7. The susceptometer of claim 4, wherein the temperature is controlled by providing a plurality of heating/cooling members coupled to the first and/or to the second case.

8. The susceptometer of claim 4, wherein the first case and the second case define a liquid gap therebetween, wherein a diathermic fluid flows through the liquid gap, thereby stabilizing the temperature within the first and the second screening regions.

9. The susceptometer of claim 1, wherein the temperature is controlled by providing a plurality of heating/cooling members coupled to the first case and by further providing temperature sensors for sensing the temperature, and wherein the temperature is adjusted by the heating and cooling members according to measurements by the temperature sensors.

10. The susceptometer of claim 9, wherein the heating and cooling members have weak magnetic properties.

11. The susceptometer of claim 1, wherein the means for processing electric signals comprise a lock-in amplifier configured for reading the electric signals, and wherein the signals are null if no sample is introduced in the first and the second screening regions.

12. The susceptometer of claim 11, wherein the means for processing further comprise a computer configured for acquiring an output signal of the amplifier in synchronism with the introduction and extraction of the sample from the first or second screening regions.

13. The susceptometer of claim 1, characterized in that it has a support structure for the magnetic field source and the first and second magnetic field sensors, including an upright, wherefrom three cantilevers project at different heights and in substantially aligned positions to support the magnetic field source and the first and second magnetic field sensors respectively.

14. The susceptometer of claim 13, characterized in that the upright and/or the cantilevers are provided as tubular or boxlike elements and may be removably fastened together by locking and/or centering means.

15. The susceptometer of claim 13, characterized in that the cantilevers are joined to the upright by means of extensions of their vertical side walls, which have the form of fastening tabs, abutting against the corresponding side walls of the upright and secured thereto by means of fast pins and dowels.

16. The susceptometer of claim 13, characterized in that the cantilevers have cavities for receiving the first and second magnetic field sensors and the magnetic field source respectively, which cavities are formed within the thickness of said cantilevers.

17. The susceptometer of claim 13, characterized in that the first and second magnetic field sensors and the magnetic field source are secured inside the thickness of the cantilevers by dowels and fast pins.

18. The susceptometer of claim 13, characterized in that the lower end upon which the upright rests, is connected to a base plate by means of trapezoidal reinforcement plates, which are fastened to said base and to the side walls of the upright.

19. The susceptometer of claim 13, characterized in that the support structure with the first and second magnetic field sensors and with the magnetic field source are accommodated in a first inner shell, which has a cavity for housing the upright which cavity communicates with three cavities for housing the cantilevers, the lower portion of the first cavity being widened to form a trapezium which corresponds to the trapezoid base of the support structure.

20. The susceptometer of claim 19, characterized in that the assembly composed of the support structure with the first and second magnetic field sensors and with the magnetic field source and its first inner shell are accommodated in a second outer shell, whose shape corresponds to that of the first inner shell, and whose size is larger to form a salable gap, through which a diathermic fluid may flow for temperature stabilization purposes.

21. The susceptometer of claim 20, characterized in that the first inner shell has two tubular supporting beams along the side walls, at the trapezoidal widened base.

22. The susceptometer of claim 21, characterized in that the two tubular support beams also act as inlets and outlets for the diathermic fluid flowing in the gap between the inner shell and the outer shell.

23. The susceptometer of claim 13, characterized in that it is provided in combination with a patient table, a stretcher, or the like, whose patient supporting surface is supported in such a manner as to be able to move vertically between the two operating positions in which the body to be screened is introduced, between the cantilever that supports the magnets and the cantilever of upper first and second magnetic field sensors and between the cantilever that supports the magnets and the cantilever of lower first and second magnetic field sensors respectively.

24. The susceptometer of claim 23, characterized in that the patient supporting surface has a cavity for accommodating the cantilever that supports the lower first and second magnetic field sensors and/or the cantilever that supports the magnetic field source.

25. The susceptometer of claim 24, characterized in that the patient table or stretcher has a base that runs on rails.

26. The susceptometer of claim 25, characterized in that the body supporting surface may be lifted or lowered with respect to the base, through a jointed arm lifting system and removable position lock means.

27. The susceptometer of claim 13, characterized in that it has three magnetic field sources each being able to generate different magnetic field flux distributions.

28. The susceptometer of claim 27, characterized in that first and second magnetic field sensors are provided on each side of the magnetic field sources, each being dimensionally adapted to the volume permeated by the magnetic flux of the corresponding magnetic field source.

29. The susceptometer of claim 28, characterized in that it has two magnetic field sources, formed by annular circular coils, which have different diameters, one being contained in the other, and are coaxial to each other and to the first and second magnetic field sensors, the latter being themselves provided as coils, one in the other and coaxial to each other, the size of concentric coils being adapted to the size of the corresponding magnetic field source.

30. The susceptometer of claim 29, characterized in that an additional magnetic field source is associated to each first and second magnetic field sensors.

31. The susceptometer of claim 30, characterized in that said magnetic field source has an annular shape and is mounted coaxially inside the smaller first and second magnetic field sensors.

* * * * *